US012562267B2

(12) United States Patent
Casati et al.

(10) Patent No.: US 12,562,267 B2
(45) Date of Patent: Feb. 24, 2026

(54) SOUND DIRECTING DEVICE FOR A MOBILE TELECOMMUNICATION DEVICE HAVING MICROBIAL BARRIER PROPERTIES

(71) Applicants: Nicolas Casati, Chicago, IL (US); Bruno Barbet, Biziat (FR); Francois Casati, Pfaffikon (CH)

(72) Inventors: Nicolas Casati, Chicago, IL (US); Bruno Barbet, Biziat (FR); Francois Casati, Pfaffikon (CH)

(73) Assignee: WOXX, INC., Chicago, IL (US)

( * ) Notice: Subject to any disclaimer, the term of this patent is extended or adjusted under 35 U.S.C. 154(b) by 396 days.

(21) Appl. No.: 17/397,792

(22) Filed: Aug. 9, 2021

(65) Prior Publication Data

US 2022/0051791 A1     Feb. 17, 2022

(51) Int. Cl.
    *G16H 40/60*        (2018.01)
    *A41D 13/11*        (2006.01)

(52) U.S. Cl.
    CPC ......... *G16H 40/60* (2018.01); *A41D 13/1138* (2013.01); *A41D 13/1161* (2013.01); *A41D 13/1192* (2013.01)

(58) Field of Classification Search
    CPC .... G16H 40/60; G16H 40/63; A41D 13/1138; A41D 13/1161; A41D 13/1192; A41D 13/1107; A62B 18/08
    See application file for complete search history.

(56) References Cited

U.S. PATENT DOCUMENTS

| | | | | |
|---|---|---|---|---|
| 3,180,333 | A | * | 4/1965 | Lewis .................... A62B 18/08 |
| | | | | D24/110.2 |
| 3,562,451 | A | * | 2/1971 | Mullen, Jr. ............. H04M 1/05 |
| | | | | 367/160 |
| 4,491,699 | A | * | 1/1985 | Walker .................... H04M 1/05 |
| | | | | 379/174 |
| 4,508,936 | A | * | 4/1985 | Ingalls .................. A62B 18/08 |
| | | | | 128/201.19 |
| 4,537,276 | A | * | 8/1985 | Confer .................. G10K 11/22 |
| | | | | 181/22 |
| 4,683,588 | A | * | 7/1987 | Goldberg ................. A41G 7/02 |
| | | | | 379/430 |
| 4,718,415 | A | * | 1/1988 | Bolnberger ............ H04R 1/083 |
| | | | | 379/430 |
| 4,856,509 | A | * | 8/1989 | Lemelson ............ A62B 23/025 |
| | | | | 128/206.16 |

(Continued)

*Primary Examiner* — Curtis J King
(74) *Attorney, Agent, or Firm* — Oliff PLC

(57)          ABSTRACT

A communication privacy device helps contain the spread of viruses, bacteria, and other microbes that spread through human respiratory infection while allowing users to utilize a cellular communication device in a private manner. The communication privacy device includes a cup-shaped mask configured to fit over a user's mouth, and a transfer tube having a first end connected to an opening of the cup-shaped mask and a second end configured to be located near a receiver of a communication device. A filter covers the opening of the cup-shaped mask. The communication privacy device allows both speaking and listening with privacy since it acts as a barrier to both the user's voice to spread in the surrounding environment and outside noises to disturb the communication.

12 Claims, 5 Drawing Sheets

(56) References Cited

U.S. PATENT DOCUMENTS

| | | | | |
|---|---|---|---|---|
| 4,980,926 A * | 12/1990 | Noetzel | A42B 3/30 | |
| | | | 381/376 | |
| 5,428,688 A * | 6/1995 | Becker | H04R 1/083 | |
| | | | 381/367 | |
| 5,503,141 A * | 4/1996 | Kettl | A62B 18/08 | |
| | | | 128/206.16 | |
| 5,933,511 A * | 8/1999 | Garth, Sr. | H04R 1/083 | |
| | | | 381/361 | |
| 6,179,666 B1 * | 1/2001 | Osborn | H04B 1/3877 | |
| | | | 439/669 | |
| 6,430,298 B1 * | 8/2002 | Kettl | A62B 18/08 | |
| | | | 381/376 | |
| 9,456,263 B1 * | 9/2016 | Oliveira | H04R 1/083 | |
| 11,305,137 B1 * | 4/2022 | McGhie | A41D 13/1192 | |
| 11,771,930 B1 * | 10/2023 | Shah | A62B 23/06 | |
| | | | 128/206.11 | |
| 2002/0166557 A1 * | 11/2002 | Cooper | H04R 1/46 | |
| | | | 128/206.28 | |
| 2005/0008183 A1 * | 1/2005 | Skillicorn | H04R 1/08 | |
| | | | 381/364 | |
| 2005/0096096 A1 * | 5/2005 | Birli | H04B 1/385 | |
| | | | 455/90.3 | |
| 2005/0201548 A1 * | 9/2005 | Birli | H04M 1/05 | |
| | | | 379/388.05 | |
| 2006/0009970 A1 * | 1/2006 | Harton | B63C 11/26 | |
| | | | 704/231 | |
| 2006/0009971 A1 * | 1/2006 | Kushner | G10L 21/0216 | |
| | | | 704/231 | |
| 2006/0057972 A1 * | 3/2006 | Wikel | H04M 1/6066 | |
| | | | 455/90.3 | |
| 2006/0121950 A1 * | 6/2006 | Lee | H04M 1/6066 | |
| | | | 455/575.2 | |
| 2006/0180153 A1 * | 8/2006 | Schaub | A62B 18/08 | |
| | | | 128/206.16 | |
| 2007/0105601 A1 * | 5/2007 | Ibbetson | H04M 1/6058 | |
| | | | 381/74 | |
| 2007/0181129 A1 * | 8/2007 | Mattinson | A62B 18/08 | |
| | | | 128/206.21 | |
| 2008/0229929 A1 * | 9/2008 | Marcoon | B01D 46/0028 | |
| | | | 264/340 | |
| 2009/0060169 A1 * | 3/2009 | Manne | H04M 1/19 | |
| | | | 379/430 | |
| 2009/0320849 A1 * | 12/2009 | Biedermann | D06M 15/263 | |
| | | | 128/206.28 | |
| 2012/0029912 A1 * | 2/2012 | Almagro | G10K 11/17823 | |
| | | | 704/226 | |
| 2013/0156246 A1 * | 6/2013 | Menyhart | H04R 1/2807 | |
| | | | 381/355 | |
| 2015/0173436 A1 * | 6/2015 | Tsuei | A41D 13/1115 | |
| | | | 2/424 | |
| 2016/0057618 A1 * | 2/2016 | Shorr | H04W 12/02 | |
| | | | 455/569.1 | |
| 2016/0072934 A1 * | 3/2016 | Moser | H04R 1/083 | |
| | | | 379/430 | |
| 2016/0174631 A1 * | 6/2016 | Tong | A01N 25/34 | |
| | | | 427/457 | |
| 2017/0368383 A1 * | 12/2017 | Riccio | A61M 16/06 | |
| 2019/0318606 A1 * | 10/2019 | Kanukurthy | G08B 21/182 | |
| 2020/0324510 A1 * | 10/2020 | Yung | B32B 5/024 | |
| 2021/0125468 A1 * | 4/2021 | Shuman | A62B 18/08 | |
| 2021/0319777 A1 * | 10/2021 | Wang | H04R 1/08 | |
| 2021/0353979 A1 * | 11/2021 | Lean | A62B 18/086 | |
| 2021/0368890 A1 * | 12/2021 | Brizuela | B32B 3/06 | |
| 2021/0386134 A1 * | 12/2021 | Plank | A41D 13/1192 | |
| 2021/0393996 A1 * | 12/2021 | Bernstein | A41D 31/30 | |
| 2021/0394197 A1 * | 12/2021 | Vanjani | A62B 18/003 | |
| 2021/0400979 A1 * | 12/2021 | Angres | A01N 59/16 | |
| 2022/0007754 A1 * | 1/2022 | Kaiserman | A41D 31/145 | |
| 2022/0070564 A1 * | 3/2022 | Riccio | H04R 1/026 | |
| 2022/0134137 A1 * | 5/2022 | Webb | A62B 9/006 | |
| | | | 128/202.22 | |
| 2022/0176168 A1 * | 6/2022 | Adams | H04R 1/083 | |
| 2022/0249884 A1 * | 8/2022 | Rathburn | A62B 23/02 | |
| 2023/0041282 A1 * | 2/2023 | Takagi | A61L 2/03 | |
| 2023/0111767 A1 * | 4/2023 | Yu | G16H 20/40 | |
| | | | 382/118 | |
| 2023/0149747 A1 * | 5/2023 | Tan | A62B 23/025 | |
| | | | 128/204.17 | |
| 2023/0181946 A1 * | 6/2023 | Kalaitzis | B01D 39/18 | |
| | | | 128/206.19 | |
| 2023/0277269 A1 * | 9/2023 | Ugbeye | A41D 13/11 | |
| | | | 128/863 | |
| 2023/0284714 A1 * | 9/2023 | Chahine | A41D 13/11 | |
| 2023/0347187 A1 * | 11/2023 | Gandrud | A62B 18/08 | |
| 2024/0108923 A1 * | 4/2024 | Mamishev | A62B 23/02 | |

* cited by examiner

SOUND DIRECTING DEVICE FOR A MOBILE TELECOMMUNICATION DEVICE HAVING MICROBIAL BARRIER PROPERTIES

INTRODUCTION

Facial masks can be used to protect the intended user and those around the user from spreading of viruses, bacteria, microbes, and the like. There is a need to continue utilizing modern technology of a cellular phone, while maintaining privacy, and preventing the spread of viruses, bacteria, microbes of the like from a user's breadth. Many pathogens are transmitted from the repertory system of a user, through the mouth, and into the public domain, where it is subsequently ingested via inhalation into a second individual. While people are utilizing a cellular phone device, there is a need for both privacy and ensuring those around the user that the user will not be spread pathogens into the public air.

With the multiplication of mobile devices, either in openspace, public locations, or the like, an effective sound-directing device will minimize voice disturbance and provide privacy to the user. Additionally, it will act as a barrier for microbes emitted by the user's mouth when speaking and being spread around. It is known that air contamination happens through tiny droplets, and/or aerosols, of infected saliva being projected and dispersed to the outside. The present sound directing device's wall is impervious as is internally lined with a cellular material acting both for sound deadening and for filtering of air. This cellular material is resistant to a chemical able to destroy viruses and may contain a biocide.

BACKGROUND

In times of pandemics, influenza seasons, and the like, in order to prevent viral and microbial infection due to airborne droplet or air blasts generated for example by sneeze, cough, or talking, masks have conventionally been used. Particularly, in order to prevent the spread of viruses like the common cold, seasonal influenza (flu), avian influenza, Coronavirus infection and the likes, strategic research and development of antibacterial masks and materials for such masks of prior art have been employed.

Microbes are tiny living creatures that can be seen only with the help of a microscope. There are four main types of such micro-organisms: bacterium, fungus, yeast and virus. While there are known methods of controlling the spreading of illnesses caused by bacteria, fungus and yeast, once these are detected, there is not such possibility with viruses because of their parasite nature. Indeed, a virus contains only one type of nucleic acid and is duplicating itself, based on its own genetic structure, by attaching itself to living cells. Of particular concern for the public health are Corona viruses, responsible for breathing or digestive infections.

It is known that a person while speaking, or coughing emits tiny drops of saliva, and that these droplets are projected to the surrounding atmosphere. It is also known that saliva of an ill person contains microbes. In addition, microbes present in throat and lungs of such an infected person can be emitted in form of aerosols, i.e. tiny particles which are suspended in the atmosphere, when air is expelled at a high enough speed, which the case with loud voice. In closed locations, such contaminated aerosols can be circulated in the surrounding through draught, ventilators, air conditioner, etc.

There is a critical time, lasting several days, called incubation time, during which a person being infected does not feel any sign of it. There is no fever, no coughing, no breathing difficulty, no skin rash, no loss of taste or smell, no tiredness. However, such infected person can contaminate unintentionally other people with his or her voice when speaking loudly during this incubation time, by projecting his or her infected saliva to the surrounding atmosphere.

Hence it is hazardous to be at close distance of such a person, being infected without knowing it, when he or she uses his or her mobile phone, which is the case, for instance, in public transportation, such as taxis, buses, trains or airplanes, and in office buildings, theaters, stadium, elevators, etc. Indeed such contaminated droplets and/or aerosols containing microbes may cause infection of people close-by either when they breath them or get skin contact with them, by various means, either direct (droplets received on face or any other body part) or indirect (contaminated cloths or touching a contaminated surface, such a door, handrail, etc).

It would be advantageous to have a facemask allowing any person, either ill or not, to use a mobile phone in public places or in offices without the risk of infecting other people present. This would allow the authorities to control efficiently contagion, i.e. the spreading of illness due to microbes, especially viruses, and more importantly retroviruses, within a population at risk. This would give a feeling of confidence for the individual leaving his or her home to go outside, for work, shopping, distractions, etc.

Additionally, it would be advantageous to have a facemask which can be used without loss of protection over time. Such a problem happens with standard surgical masks, made of fabric, which are prone to get wet due to moisture coming from the user's mouth when breathing. Once humid, these surgical masks lose most of their filtration capabilities and need to be replaced. In addition, standard surgical masks act as a barrier for the voice when the person wearing them uses their phones. Hence these persons tend to speak louder and are more disturbing for their neighborhood.

To combat the spread of viruses described above, antimicrobial masks, like those described in the withdrawn application by Ishgami, et al EP 207056A1, disclose the use of synthetic fibers having silver-plated or deposited surfaces, mask filters comprising antimicrobial changed filter obtained in form of the electric fiber and ground fabric has been treated with dispersion liquid containing antimicrobial particles such as supported inorganic silver particles so that these antimicrobial particles may adhere to the fiber surface of the ground fabric and the antiviral mask comprising fibrous substrate having hydroxy and simultaneously including hydroxyl group and carboxyl group such as citric acid, malic acid or lactic acid fixed thereto.

Though these masks are useful for the sole and only purpose to the user as a means to prevent the spread of said viruses, they masks fail to contemplate the necessity for the user to utilize a cellular phone device in a private setting. Privacy of communication is an important and essential part of utilization of a cellular device.

In view of the problem as described above, it is a principle object of the present invention to provide a mask that utilizes materials that absorb sound and droplets of fluid from a users mouth while transmitting the sound vibrations down a tube and then received on a cellular device. The contemplated material exhibits high affinity to fluid droplets exhausted from a user's mouth containing droplets that carry a transmittable virus.

The acoustical advantages of a privacy mask, with elongated mouth-piece, having a semi-circular opening for a user's mouth and a second opening coupled with a transfer tube in which a user's voice travels until it reaches the receiver of a mobile phone or computer, inserted in a head-set equipped with ear-pieces, have been presented in Casati, et al, US 2020/0029144A1.

The acoustical privacy mask contemplated by Casati failed to contemplate the necessity of trapping microbes emitted by the user's mouth while speaking and being made of materials that are specific to prevent the spread of contagious diseases, like the Influenza and Corona (Covid-19) virus.

In the past, built-in embedded microphone to a mask taught that sterility regulations in surgical settings do not allow for such masks, Cooper, US Appl. 2002/0166557A1. Cooper continues to disclose that sterilization or barrier protection is required for use of a separate microphone system with a mask, and in surgical applications, a headset mounted microphone is not only dangerous, but is often impractical.

A respirator for protection against droplet infections, comprising at least a mouth area of a person covering the filter surface by electrolysis of sodium chloride solution is contemplated in the German application by Gleich, DE 102016002826.2A. In Gleich, the invention relates to protection against droplet infection respirator mask. The invention solved the problem that the respirator is additionally equipped with an absorber for receiving the sodium hypochlorite solution. The voice receiver then transmitted the electric signal down a sterilized cable to a transmitter.

U.S. Pat. No. 5,727,54 A relates to a respirator with gauze filter surface known. The respirator has a user's nose covering portion which serves to maintain the face temperature in the nose area.

Korean application KR 102005012235A discloses a protective respirator configured to enable an operator to easily communicate while the body is not exposed to a hazardous environment. The invention discloses a voice diaphragm, an oxygen supply unit and a connection string include a wireless communication terminal mounted on the front face of the voice diaphragm to enable two-way communication between the wearer and a third party.

It is important to point out that the device claimed in US 2020/0029144A1 is made with a cup-shaped mask having an impervious wall surface, as it is required to reduce voice sound, which is not sensitive to moisture. Hence this device is an effective barrier for microbes emitted by the user whatever its type of carrier, either saliva droplets or aerosols. A foam layer, or interliner, placed within the inner surface of the device to improve acoustics, especially to avoid echo, is also not sensitive to moisture.

The present invention is an improvement over US 2020/0029144A1 as it includes air filters, with high filtration capability, at all openings of such a device. In addition, the disclosed foam interliner being a cellular material may contain biocides, fungicides, bactericides, or the like.

The present invention is a telecommunication device allowing both speaking and listening with privacy, since it prevents both the user's voice to spread in the surrounding and outside noises to disturb the communication, this device having air breathing openings equipped with filters to trap potential contaminated saliva droplets. Such filters are made of cellular material covered with a piece of fabric, or disposable paper. This cellular material, having a minimum thickness of 0.5 centimeter and a density between 5 and 150 kg/m3, is made of materials resistant to a chemical able to destroy viruses.

The cellular material is filled with an antimicrobial agent either during manufacturing or through a post-treatment such as dipping in a liquid containing such antimicrobial agent. The cellular material can also be treated with an antimicrobial agent after usage of the device claimed with US 2020/0029144A1, in order to eliminate potential contamination. Hence it is not anymore hazardous and can potentially be reused without harm. Antimicrobial agents may be biocides, such as fungicides or bactericides. One example of fungicide is Amical 48* by Angus, containing Iodine. Antimicrobial agents may be chemical agents such as Chlorine solutions or hydro-alcoholic gels, based on ethanol or isopropyl alcohol and glycerol, as recommended by the WHO, or World Health Organization. For viruses, such hydro-alcoholic gels are effective to destroy viruses. Said hydro-alcoholic gel may also contain oxygenated water.

Other means to eliminate viruses are for instance heat, UV radiations or exposure to certain gases, such as ethylene oxide. However such treatments require special equipment not available on the spot, while a chemical can be transported in a proper container, either a bottle or a sprayer, and be used anywhere to decontaminate the device claimed with US 2020/0029144A1.

It is contemplated that the device claimed with the present invention can be applied against the user's cheek skin to prevent outside contamination. It can be held in position in front of the user's mouth through all possible means including a belt, straps, headband, spectacle arms, etc.

It is contemplated that to prevent direct contact of the device with user's skin is to have a disposable protective layer and/or film, made of fabric, paper, non-woven or felt. It is contemplated that the opening of the device where a user places his or her face is equipped with a cushion made of cellular material, or foam, having open cells and being protected with a cover. Such flexible foam has open cells, preferably over 95% open cells, to allow the user's breathing and to avoid moisture build up inside the device. The cushion's cover is also breathable. It could be made for instance of fabric. The cushion can be removable and washable. Such a cushion acts as filter for saliva droplets emitted by the speaker. Additionally, such a cushion, having a minimum thickness of 0.5 centimeter is effective to compensate for differences in the features of user's face since it needs to fit all types of users.

It is contemplated that there are several sizes for the device, smaller ones for young people, larger ones for older ones. It is contemplated that the users of the privacy speaking device may breathe freely through proper openings either in the mask or mouthpiece, or at the end of the outside tube. In case of openings, these are equipped with filters, such a fabric or non-woven. Preferably a layer of foam, or cellular material, is also present. The whole combination foam and cover has superior filtering capability for infected saliva droplets.

It is contemplated that the foam interliner is not glued to the mask or mouthpiece, hence can be removed and replaced after extensive use to preserve hygiene. It can also be decontaminated with proper chemicals.

It is contemplated that the foam interliner can be kept out of direct contact with the mouth through the use of a disposable protective layer and/or breathable film that is able to withstand moisture. As it is mentioned in paragraph 20 of US 2020/0029144A1, the device may or may not cover the nose of the user. However, in case of protection against microbes coming from the outside, it may be advisable to have a device made of impervious material covering the nose, provided, as described heretofore, proper breathing openings are present.

A hydro-alcoholic gel containing 75% by volume Isopropanol and about 1.5% glycerol, known to kill viruses, is poured on a piece of cellular material made of Melamine having a thickness of 0.5 centimeter and a density around 10 kg/m3. The foam absorbs quickly, like a sponge, the hydro-alcoholic solution without losing its integrity and without swelling. After a couple of hours at room temperature, the cellular material is again dry, has fully recovered its hardness and shows no loss of tensile strength. More importantly no cells were damaged. Such a cellular material does not contain viruses and can be used again as interliner with the device claimed with the present invention.

Preferably the device claimed in US 2020/002144A1 is combined with a surgical mask, made of fabric, which covers user's nose, cheeks and chin, as per FIG. 1. Such a surgical mask, with high filtration capability for small particles, contains a hole to insert the sound controlling device and can be replaced after use. It is equipped with proper means to be held against the user's skin, such as belt, straps, headband, spectacle arms, etc. It is designed to avoid any leakage at the junction between the mask and the device, as it is also a mean to protect the user against projection from the public nearby.

It is contemplated that the surgical mask has only a hole for the transfer tube of the device and covers the mask itself as shown in FIG. 2. This allow the mask to be protected against contamination from the outside. The transfer tube may be disposable after being removed.

It is contemplated that the second opening of the device is connected to the receiver of a mobile phone or computer, inserted in a head-set equipped with ear-pieces as shown in FIG. 3.

It is preferred to have one disposable protective layer or film for the whole device that can be left in place when the phone is not needed, in order to protect its surface from outside contamination. Another option is to place the whole device in a bag. When the device of US 2020/002144A1 is not needed, the user can replace it with a conventional surgical mask to maintain his or her protection.

DETAILED DESCRIPTION

Figure 1:
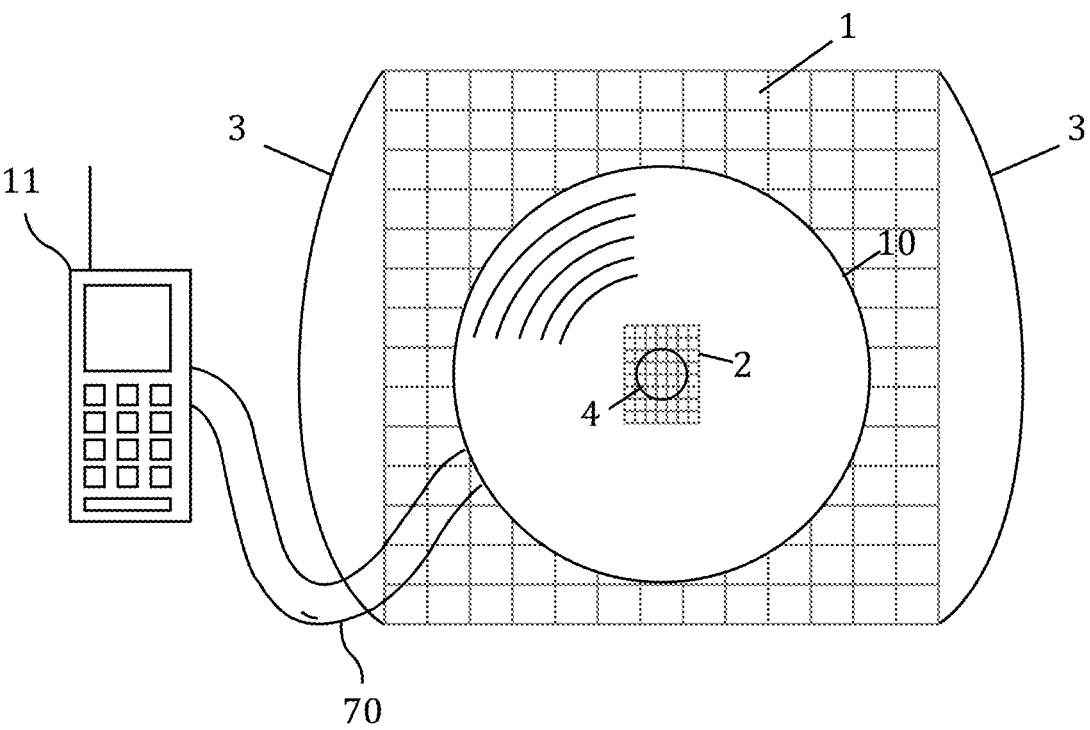
FIG. 1 shows an embodiment of a communication privacy device and a communication device.

Referring to FIG. 1, the mask 10 has an opening 4 connected to an exit tube 70 with a filter 2 made of fabric. The whole device is inserted in a hole present at the center of the surgical mask 1. The surgical mask is equipped with straps 3 designed to hold it against the user's face by placing them behind user's ears. The transfer tube 70 distal end is located at or near communication device 11.

Figure 2:
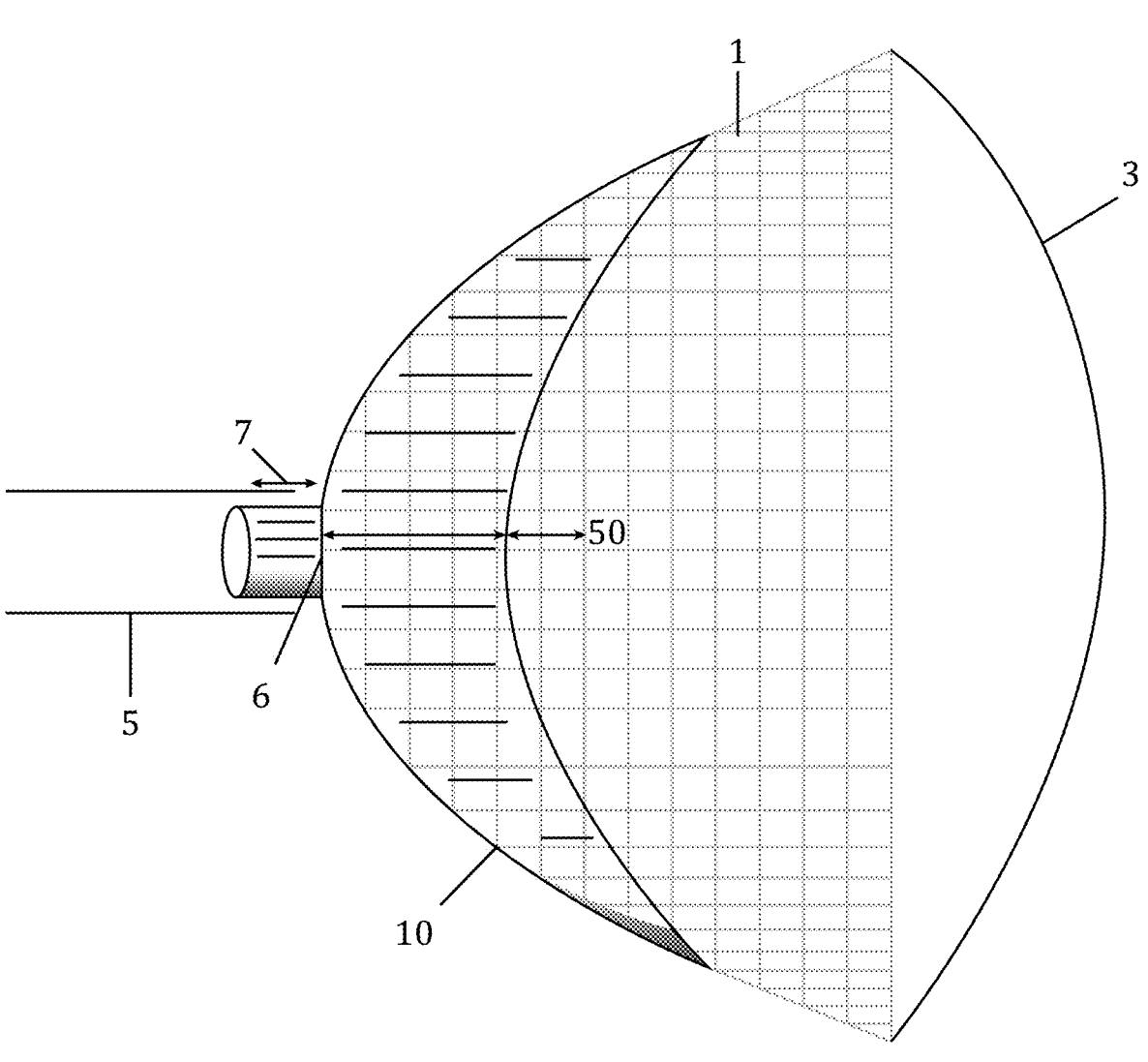
FIG. 2 shows a side view of a communication privacy device.

Referring to FIG. 2, the mask 50 is covered with the surgical mask 1, equipped with straps 3 and hole 6 at exit 7. The transfer tube 5 is adjusted to exit 7 and can be removed.

Figure 3:
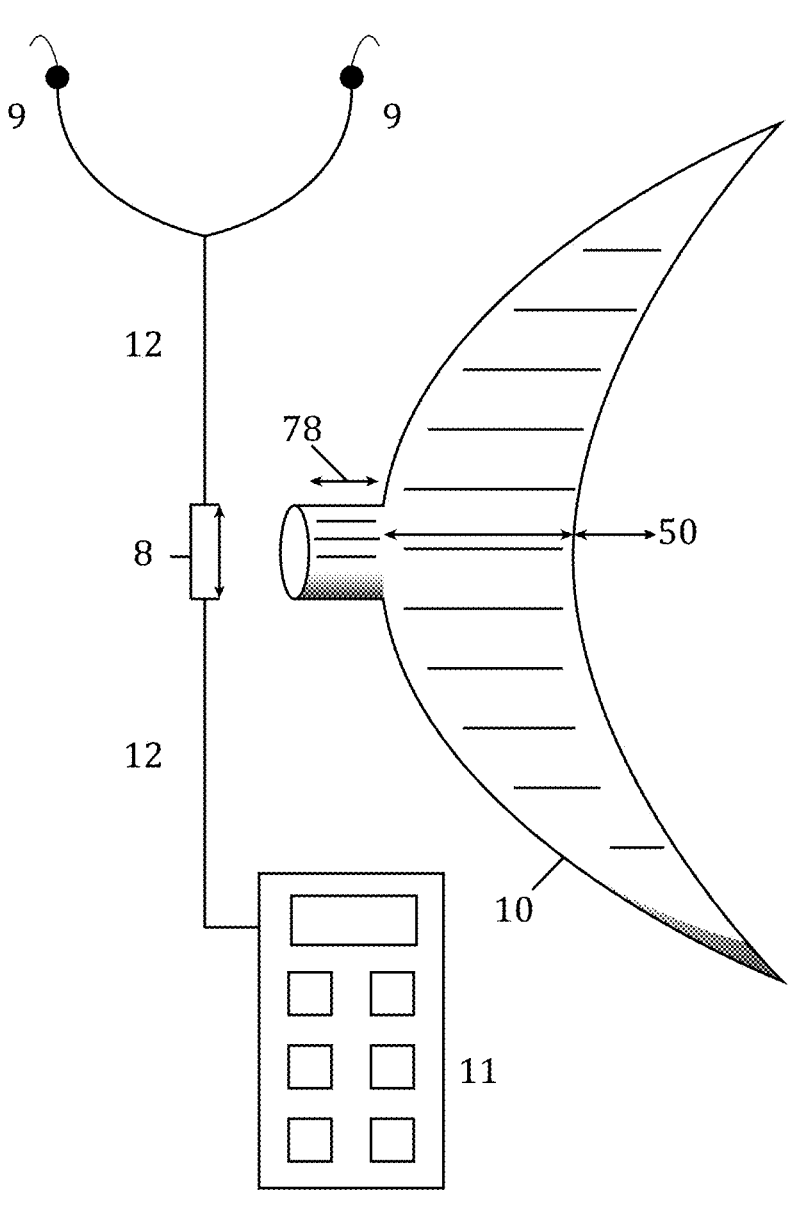
FIG. 3 shows a side view of a mask portion of a communication privacy device placed near a receiver of a mobile phone.

Referring to FIG. 3, the second opening 78 of mask 50 is connected to the receiver 8 of a mobile phone 11 equipped with ear-pieces 9 through cable 12.

Figure 4:
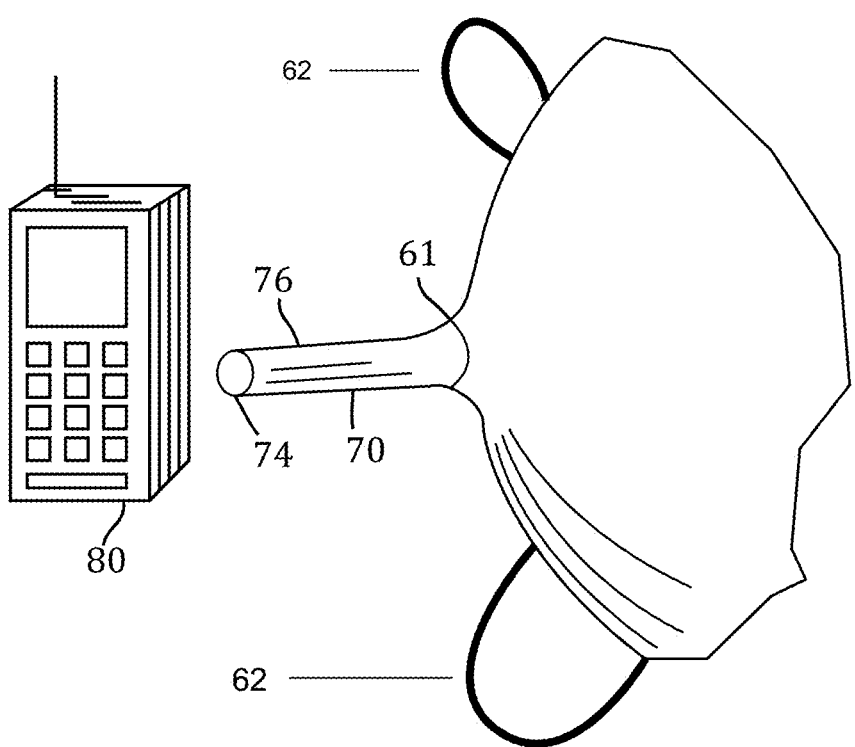
FIG. 4 shows an embodiment of a communication privacy device and a cellular device.

Referring to FIG. 4, the mask 50 has ear lobe attachment appendages 62 located on both sides of mask 50. The transfer tube opening 61 is located at the connective point between mask 50 and tube 70. The sound is directed to opening 74 at or near the cellular device 80.

Figure 5:
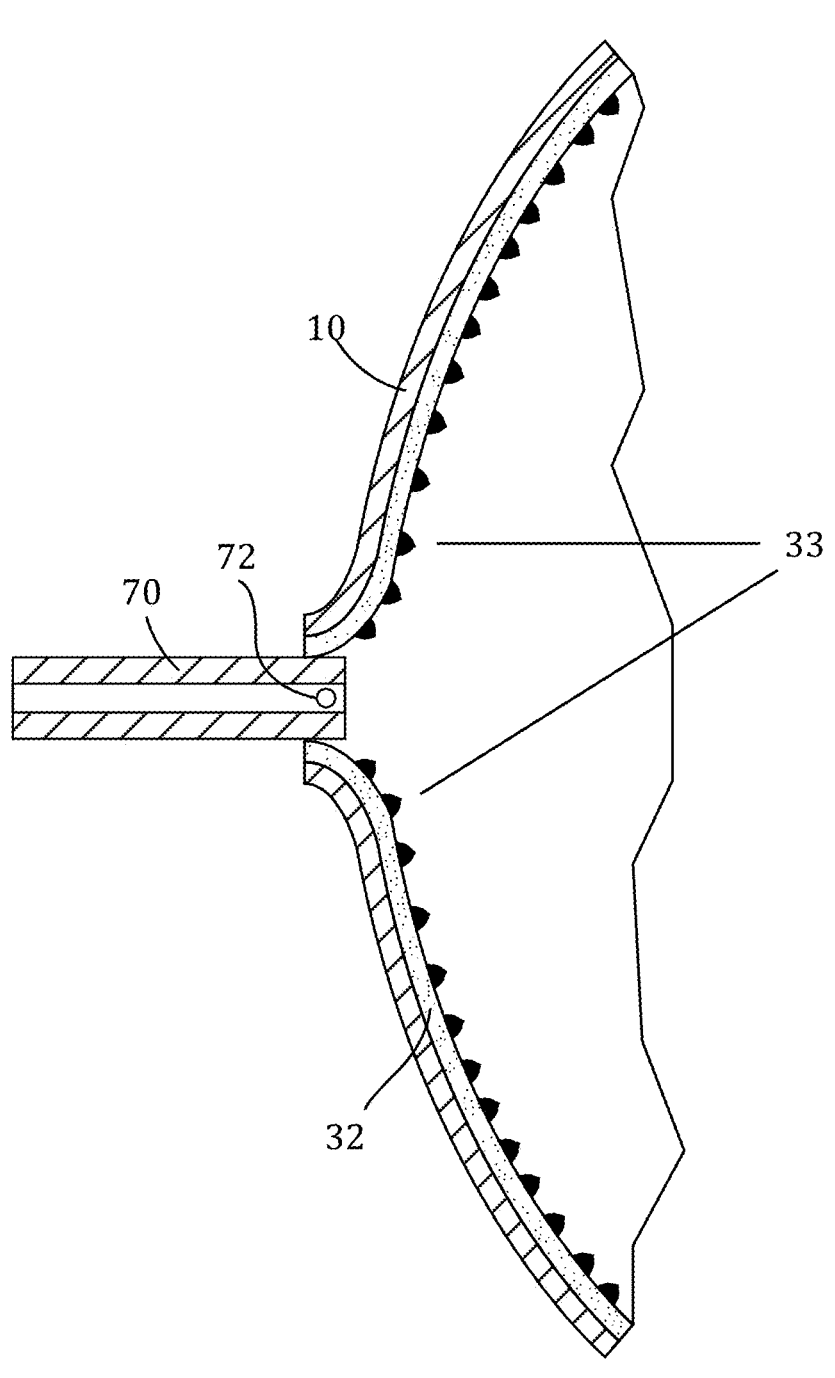
FIG. 5 shows a partial side view of an interior of a communication privacy device.

Referring to FIG. 5, in the interior of the mask is location of anti-viral material or foam material 33 with an irregular top surface increasing noise absorption along the inside of mask 10.

The invention claimed is:

1. A communication privacy device, comprising:
   a cup-shaped mask configured to fit over a user's mouth and having (i) an inner wall surface, (ii) an outer wall surface, and (iii) an opening;
   a noise absorbing material lining the inner wall surface;
   a transfer tube having (i) only two openings, (ii) a continuous inner surface, (iii) a continuous outer surface, (iv) a first end connected to and in communication with the opening of the cup-shaped mask, and (ivy) a second end configured to be located near a receiver of a mobile phone, intelligent personal assistant or computer, the transfer tube being open to atmosphere at the second end and configured to convey sound to the receiver via an air gap located between the second end and the receiver; and
   a filter covering the opening of the cup-shaped mask.

2. The communication privacy device described in claim 1, further comprising a surgical mask, made of filtering material, configured to cover the user's nose, chin and cheeks, the surgical mask covering the cup-shaped mask and being larger than the cup-shaped mask, and having a hole through which the transfer tube passes.

3. The communication privacy device described in claim 2, wherein the cup-shaped mask is made of impervious material and the noise absorbing material is a foam layer with open cells.

4. The communication privacy device described in claim 1, wherein the transfer tube is disposable.

5. The communication privacy device described in claim 1, wherein the noise absorbing material is made of Melamine cellular material and is resistant to a chemical able to destroy viruses.

6. The communication privacy device described in claim 5, wherein the Melamine has absorbed a hydro-alcoholic gel as the chemical able to destroy viruses.

7. The communication privacy device described in claim 1, wherein the second end of the transfer tube is connected to the receiver of the mobile phone, intelligent personal assistant or computer, and the mobile phone, intelligent personal assistant or computer is equipped with ear-pieces.

8. The communication privacy device of claim 1 in combination with the mobile phone, smart phone, intelligent personal assistant or computer.

9. The communication privacy device described in claim 1, further comprising an anti-viral material.

10. The communication privacy device described in claim 1, wherein the cup-shaped mask is made of impervious material and the noise absorbing material is a foam layer with open cells.

11. The communication privacy device described in claim 1, wherein the communication privacy device has a size selected for a particular user.

12. A method of communicating through a communication privacy device, the communication privacy device comprising:

a cup-shaped mask configured to fit over a user's mouth and having (i) an inner wall surface, (ii) an outer wall surface, and (iii) an opening;

a noise absorbing material lining the inner wall surface;

a transfer tube having (i) only two openings, (ii) a continuous inner surface, (iii) a continuous outer surface, (iv) a first end connected to and in communication with the opening of the cup-shaped mask, and (v) a second end configured to be located near a receiver of a mobile phone, intelligent personal assistant or computer, the transfer tube being open to atmosphere at the second end and configured to convey sound to the receiver via an air gap located between the second end and the receiver; and a filter covering the opening of the cup-shaped mask, the method comprising:

positioning the second end of the transfer tube of the communication privacy device near the receiver, without physical connection to the receiver, and conveying sound to the receiver via the air gap, the air gap being open to atmosphere.

* * * * *